(12) United States Patent
Jesenko

(10) Patent No.: US 9,519,991 B2
(45) Date of Patent: Dec. 13, 2016

(54) METHOD FOR DISPLAYING OPTICALLY DETERMINED SURFACE GEOMETRIES

(71) Applicant: Jurgen Jesenko, Finkenstein (AT)

(72) Inventor: Jurgen Jesenko, Finkenstein (AT)

(73) Assignee: A. TRON3D GMBH, Klagenfurt am Worthersee (AT)

( * ) Notice: Subject to any disclaimer, the term of this patent is extended or adjusted under 35 U.S.C. 154(b) by 44 days.

(21) Appl. No.: 14/372,282

(22) PCT Filed: Feb. 4, 2013

(86) PCT No.: PCT/AT2013/000016
§ 371 (c)(1),
(2) Date: Jul. 15, 2014

(87) PCT Pub. No.: WO2013/116879
PCT Pub. Date: Aug. 15, 2013

(65) Prior Publication Data
US 2015/0009210 A1 Jan. 8, 2015

(30) Foreign Application Priority Data

Feb. 6, 2012 (DE) .......................... 10 2012 100 959

(51) Int. Cl.
*G06T 15/00* (2011.01)
*A61B 5/107* (2006.01)
*G01B 21/04* (2006.01)
*G01B 11/25* (2006.01)
(Continued)

(52) U.S. Cl.
CPC ............. *G06T 15/00* (2013.01); *A61B 5/1077* (2013.01); *A61B 5/1079* (2013.01); *A61B 5/7221* (2013.01); *A61B 5/742* (2013.01); *A61C 9/0053* (2013.01); *G01B 11/25* (2013.01);
(Continued)

(58) Field of Classification Search
None
See application file for complete search history.

(56) References Cited

U.S. PATENT DOCUMENTS

2004/0264625 A1* 12/2004 Basu .................. A61B 6/032
378/4
2007/0172112 A1 7/2007 Paley et al.
(Continued)

FOREIGN PATENT DOCUMENTS

AT 508 563 2/2011

OTHER PUBLICATIONS

International Search Report dated May 10, 2013, corresponding to PCT/AT2013/000016.

*Primary Examiner* — Andrew G Yang
(74) *Attorney, Agent, or Firm* — Young & Thompson

(57) ABSTRACT

In a method for displaying at least one property of an optically determined surface geometry of at least one three-dimensional object, in particular a tooth, on a display, in particular a computer screen, a defined region of the surface geometry is monitored to ascertain whether a defined criterion has been fulfilled. An amount of optically determined data of the defined region is a criterion. A number of defined regions of the surface geometry are assigned a property when all the regions of the number meet the criterion. The property is displayed graphically in a defined manner, wherein different properties are graphically displayed in a differing manner.

2 Claims, 2 Drawing Sheets

(51) Int. Cl.
*A61B 5/00* (2006.01)
*A61C 9/00* (2006.01)

(52) U.S. Cl.
CPC .......... *G01B 11/2513* (2013.01); *G01B 21/04* (2013.01); *G01B 21/047* (2013.01)

(56) References Cited

U.S. PATENT DOCUMENTS

| | | | |
|---|---|---|---|
| 2011/0187824 A1* | 8/2011 | Hori | H04N 13/00 348/45 |
| 2012/0065756 A1* | 3/2012 | Rubbert | A61C 5/007 700/98 |
| 2012/0218389 A1 | 8/2012 | Nowak et al. | |

* cited by examiner

METHOD FOR DISPLAYING OPTICALLY DETERMINED SURFACE GEOMETRIES

BACKGROUND OF THE INVENTION

Field of the Invention

The invention relates to a method for displaying at least one property of an optically determined surface geometry of at least one three-dimensional object, especially a tooth, on a display, in particular a computer screen.

This method is known from, for example, AT 508 563 B. In this case, the area of application of the invention extends to digital recording of tooth and jaw impressions, assistance in diagnosis, supervision of tooth treatments, and reliable monitoring of inserted implants. In addition to further applications in the field of medical and industrial technology, for example in the field of endoscopy, objects that are poorly accessible can also be stereometrically measured and displayed.

Description of the Related Art

The disadvantage here is that a three-dimensional geometry is displayed, but no further information is made available to the user that is useful to him in the handling of the device as support for obtaining surface geometries that are as exact as possible.

The object of the invention is therefore to improve the display of optically determined surface geometries such that additional information is made available to the user that facilitates handling for him such that he can improve the detected surface geometry, depending on the requirement, completely or else only in regions, in a controlled manner.

BRIEF SUMMARY OF THE INVENTION

This object is achieved with a method of the initially named type in that for a defined region of the surface geometry, it is checked whether a defined criterion is satisfied, in that a number of optically determined data of the defined region is a criterion, in that a property is assigned to a set of defined regions of the surface geometry if all regions of the set meet the criterion, in that the property is graphically displayed in a defined manner, and in that different properties are graphically displayed differently.

A set is defined here in the mathematical sense; therefore, it can also contain, for example, only one member. An empty set in this sense would also be conceivable, but would not make any technical sense since a property can no longer be assigned to the set without members.

According to one preferred embodiment of the invention, the surface geometry is detected by means of stereometry. The latter is especially well suited to the method since here, based on the transform matrix by which recorded two-dimensional data are converted into a three-dimensional surface geometry, more data of a region of the surface geometry also always lead to more accuracy.

In another preferred embodiment of the invention, the graphic display of different properties takes place by different colors. This is especially advantageous since colors in general already can be intuitively grasped without a key or instruction for interpretation. One simple example is the association of green with "good" and red with "bad." Thus, for example, sets of regions with a large number of data, therefore high accuracy, can be displayed in green, and sets of regions with a small number of data can be displayed in red. If, for example, regions are colored red, the user acquires therefrom the information that further data are required here; he must therefore record the region, for example, once again in order to achieve the desired recording accuracy. In addition or alternatively, a color can also be determined with which it is signaled to the user that in the pertinent region, optimum accuracy has already been reached; further recordings therefore no longer produce any noteworthy improvement of the accuracy of the displayed surface geometry. Of course, other types of display are also conceivable. Thus, for example, regions that have reached a desired accuracy can be represented or characterized by check marks.

According to another preferred embodiment of the method according to the invention, the number can be the sum of pixels of the defined region. Therefore, the resolution of a region becomes a criterion in this way.

According to one especially preferred embodiment of the invention, the regions are individual voxels, therefore volume pixels, of the surface geometry. Therefore, in this case, for example, for sets with only one member, the voxel itself could be colored in order to reproduce the property. For sets with more than one member, for example, a set would be conceivable that comprises all voxels of a tooth. In this case, an additional display outside the display of the actual surface geometry would be conceivable. Thus, for example, surfaces or objects on one edge of the display could be representatively colored or in some other way could be graphically altered if the number of data as a criterion for all voxels of a tooth is satisfied.

According to a quite especially preferred embodiment of the invention, the number is the sum of the updatings of the defined region. Updating is defined here as an improved definition of the region, for example by repeated scans by means of at least one camera. Since in stereometric methods, more data arise by more updatings and the latter lead to more accuracy, direct assignment of the number of updatings to the graphic display is an especially simple route that thus especially saves resources for a computer unit in order to display a property of an optically determined surface geometry.

In one simple example in which, for example, only the number of updatings that were made from a defined region is the criterion, for example 7 or more updatings can be regarded as optimum. Sets with regions of which therefore at least 7 updatings have already been made can be assigned the property "optimum," and this property can, for example, be displayed in white. In order to achieve the desired quality of the recording, for example the property "good," for example 5 to 6 updatings may already be sufficient. Sets with regions, of which therefore 5 to 6 updatings have been made, could be displayed, for example, green. Sets of regions, of which for the desired quality only an insufficient number of updatings has been made, to which therefore, for example the properties "insufficient" or "defective" could be assigned, could be displayed, for example, in red or blue. Blue here would stand for the somewhat better quality of 3 to 4 updatings, therefore the property "defective." Accordingly, sets of regions could be displayed red, of which only 1 to 2 updatings have been made, to which therefore the property "insufficient" has been assigned. Sets of regions, of which no updating at all has been done but which are still displayed (for example by extrapolation), could be assigned for example the property "empty" that could, for example, be displayed black.

It is first determined according to the invention how many recorded data altogether are available for a defined region of the determined surface geometry. In this case, the definition of the regions takes place, for example, via the subdivision of the recording into so-called voxels or groups of voxels, for example 40 voxels. Alternative region definitions that, for example, result from patterns that have been projected or in some other way applied to the object for supporting the optical determination of the surface geometry of an object are likewise conceivable.

Embodiments that in addition or alternatively calls [sic] for another graphic display as different colors, therefore, for example, different intensities of one and the same color or different graining, are likewise within the scope of the invention.

Other preferred embodiments and implementations of the invention are the subject matter of the other dependent claims.

BRIEF DESCRIPTION OF THE DRAWINGS

The invention is further explained below with reference to the drawings. Here.

DETAILED DESCRIPTION OF THE PREFERRED EMBODIMENTS

Figure 1:
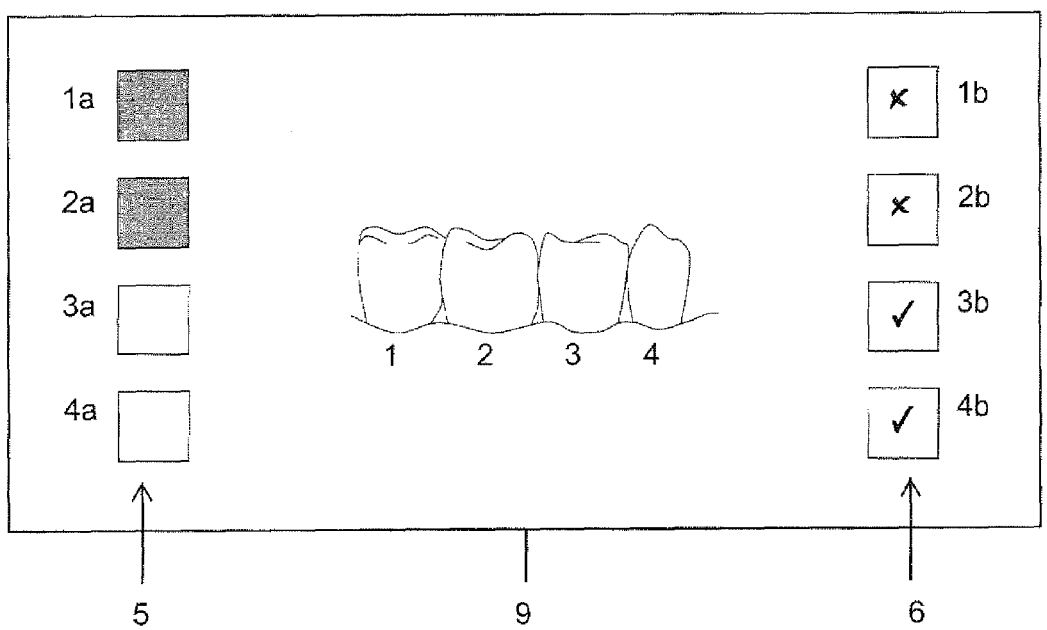
FIG. 1 shows a group of teeth with two representative displays of teeth, which can be displayed individually or jointly.

FIG. 1 shows one embodiment of the invention in which three-dimensional objects 1, 2, 3, 4 whose surface geometry is being determined are teeth, with two possible representative displays 5, 6, the set of defined regions being the set of all voxels of one tooth at a time. This is imaged on a display 9. In doing so, the smallest number of optically determined data that are necessary for a desired accuracy is defined as a criterion. Thus, when the desired accuracy is reached in a first representative display 5, for example, quadrilaterals 1a, 2a, 3a, 4a that represent the teeth 1, 2, 3, 4 can change their color. In the illustrated example, the first and second tooth 1, 2 have not yet reached the desired accuracy. The representative first two quadrilaterals 1a, 2a are displayed in the drawing in gray, on the actual screen however, for example, in red. For the third and fourth tooth 3, 4, the criterion is already satisfied; the representative quadrilaterals for these teeth 3a, 4a are displayed in the drawings in white, but, for example, in green on the actual screen. Analogously, in one alternative second representative display, quadrilaterals 1b, 2b, 3b, 4b are provided with check marks or X. The most varied embodiments in which, for example, numbers instead of colors represent the accuracy of the recording, therefore, for example, a scale from 1 to 10, or in which instead of quadrilaterals 1a, 2a, 3a, 4a, 1b, 2b, 3b, 4b, more vivid representations of the objects, for example tooth-shaped surfaces, are chosen, are likewise within the scope of the invention. Alternatively or additionally, as can be seen in FIG. 2, the displayed objects 1c, 2c, 3c, 4c themselves can also be colored.

Figure 2:
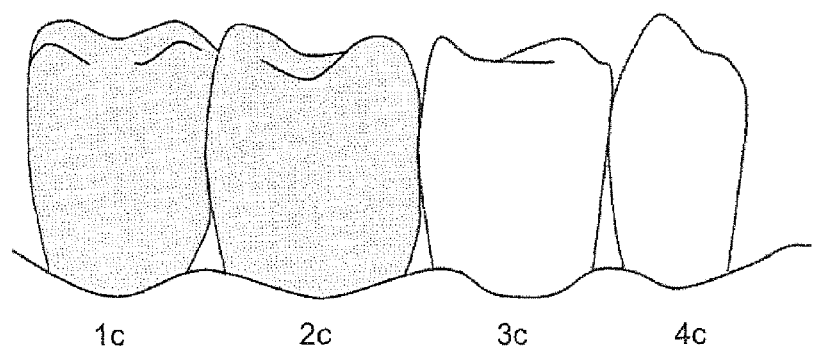
FIG. 2 shows the group of teeth partially colored.
Figure 3:
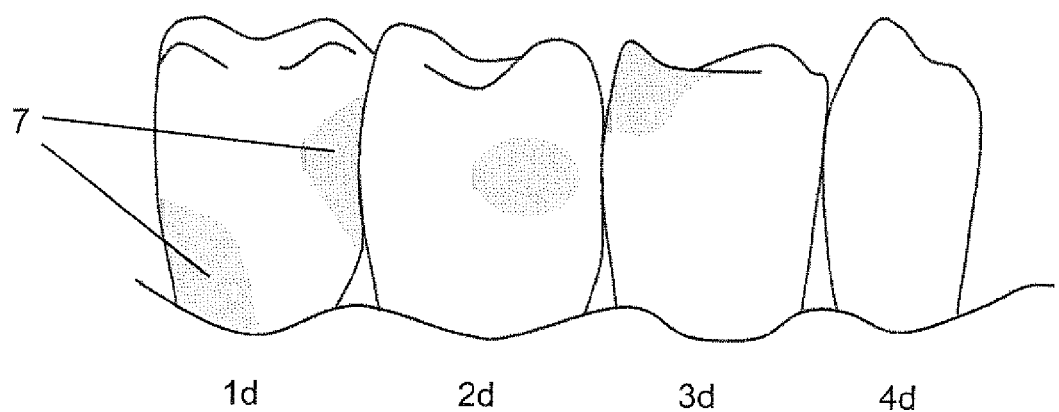
FIG. 3 shows the group of teeth with an alternative type of coloring.
Figure 4:
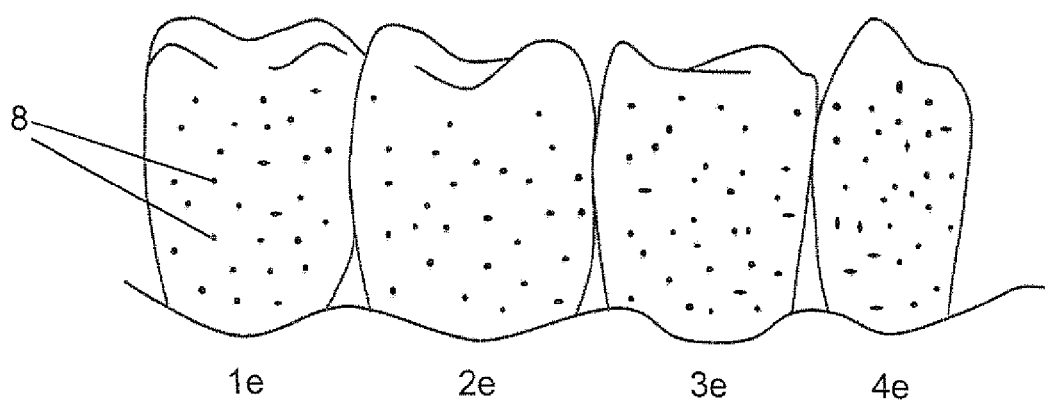
FIG. 4 shows the group of teeth with a third type of coloring.

FIGS. 3 and 4 show embodiments in which, similarly to FIG. 2, the displayed geometry itself is colored. In any case, the sets contain fewer members. Thus, as shown in FIG. 3, for example, sections 7 of objects 1d, 2d, 3d, 4d can be colored; this makes the handling instruction for the user more precise. Instead of an instruction as to which teeth are to be still better detected, he now acquires the more exact instruction, for example which regions or from what direction he must continue to acquire the objects in order to arrive at the desired accuracy.

FIG. 4 shows one embodiment in which the sets have been limited to individual voxels 8. The user therefore acquires similar instructions as in FIG. 3, only with still more details. In embodiments in which more criteria than the two shown by way of example are defined, the handling instruction is accordingly more comprehensive.

The invention claimed is:

1. A method for displaying at least one property of an optically determined surface geometry of a tooth on a computer screen, the method comprising the steps of:

repeatedly scanning the tooth using a stereometry camera, checking the surface geometry of the tooth, and determining whether one of plural defined criteria is satisfied for each voxel of the surface geometry of the tooth, each voxel being a volume pixel representing a smallest unit within a computational three-dimensional volume, said checking including updating of optically determined data of each voxel, wherein at least a first of the defined criteria is a first sum of the updatings of the optically determined data of each specific voxel, and a second of the defined criteria is a second sum of the updatings of the optically determined data of each specific voxel;

assigning at least a first property to voxels satisfying the first criteria, and assigning a second property to voxels satisfying the second criteria, to thereby define all of the voxels are divided into respective sets with a first set of voxels that each satisfy the first criteria and a second set of voxels that each satisfy the second set of criteria; and graphically displaying the surface geometry on the tooth on the computer screen, with at least the voxels of the first set assigned with the first property being graphically displayed differently from the voxels of the second set assigned with the second property.

2. The method of claim 1, wherein the voxels of the first set assigned with the first property are graphically displayed in a first color and the voxels of the second set assigned with the second property are graphically displayed in a second color.

* * * * *